United States Patent [19]

Ray

[11] Patent Number: 4,688,939
[45] Date of Patent: Aug. 25, 1987

[54] METHOD AND APPARATUS FOR INSPECTING ARTICLES

[75] Inventor: Rajarshi Ray, Princeton, N.J.

[73] Assignee: AT&T Technologies, Inc., Berkeley Heights, N.J.

[21] Appl. No.: 813,747

[22] Filed: Dec. 27, 1985

[51] Int. Cl.$^4$ .......................................... G01N 21/88
[52] U.S. Cl. .................................. 356/237; 250/562; 250/572; 358/106
[58] Field of Search ................ 356/237; 250/562, 572; 358/106

[56] References Cited

U.S. PATENT DOCUMENTS 4,028,728  6/1977  Sharp ..................................... 358/106
4,343,553  8/1982  Nakagawa et al. ................. 356/376

OTHER PUBLICATIONS

Sterling, "Nonreference Optical Inspection of Complex and Repetitive Patterns" *Proc. SPIE*, vol. 281, pp. 182–190, 1981.
Y. Nakagawa, "Automatic Visual Inspection of Solder Joints on Printed Circuit Boards" in *Proc. SPIE*, Robot Vision, vol. 336, May 1982, pp. 121–127.
W. E. McIntosh, "Automating the Inspection of Printed Circuit Boards," *Robotics Today*, Jun. 1983, pp. 75–78.
G. J. Lemay, et al., "The Role of Illumination in the Inspection of Solder Joints," Report 19, Robotics Research Center, University of Rhode Island, Aug. 1983.
M. P. Seah et al., "Certainty of Measurement Using an Automated Infra-Red Laser Inspection Instrument for PCB Solder Joint Integrity, *Journal Phys. E: Sci. Instrum.*, vol. 18, 1985, pp. 676–683.
C. Lea et al., "Automated Inspection of PCB Solder Joints, An Assessment of the Capability of the Vanzetti LI-600 Infra-Red Laser Inspection Instrument," *Brazing and Soldering*, No. 8, Spring 1985, pp. 34–42.
R. Pound, "Inspection Equipment Exposes Quality of Soldered Joints," *Electronic Packaging & Production*, Feb. 1986/85, pp. 84–86.
IRI Model P 256 Vision System Instruction Manual, published by IRI, Carlsbad, CA (1982), pp. 3–114.
*Robot Vision*, by B. K. P. Horn (The MIT Press/McGraw-Hill Book Company, 1986), pp. 53–55.
*Computer Vision*, by B. Ballard et al., (Prentice Hall, 1982), pp. 56–59.
"High-Speed Automatic Particle Counter" by Shaw & Sopher, IBM Technical Disclosure Bulletin, vol. 17, No. 9, Feb. 1975, p. 2588.
"Surface Defect Detector," E. E. Haas et al., Western Electric Technical Digest, No. 25, Jan. 1972, p. 37.
"Automatic Visual Solder Joint Inspection" by P. J. Besl et al., IEEE Journal of Robotics and Automation, vol. RA-1, No. 1, pp. 42–56.

*Primary Examiner*—Davis L. Willis
*Assistant Examiner*—Matthew W. Koren
*Attorney, Agent, or Firm*—R. B. Levy

[57] ABSTRACT

Automated inspection of solder bumps (18—18) on a major surface (14) of a chip carrier (10) is accomplished by placing the chip carrier on a platform (22) beneath a ring light (28) which is in registration with a television camera (30). Light from the ring light, which is directed at an angle towards all sides (12—12) of the chip carrier, is only reflected upwardly into the television camera by the solder bumps. The output signal of the television camera, which varies with the intensity of the light reflected from the solder bumps, is processed by a vision system (32) to obtain a one-dimensional plot of the light intensity. The one-dimensional intensity plot is analyzed automatically by the vision system to detect for missing, bridged or excessive solder bumps on the chip carrier.

13 Claims, 6 Drawing Figures

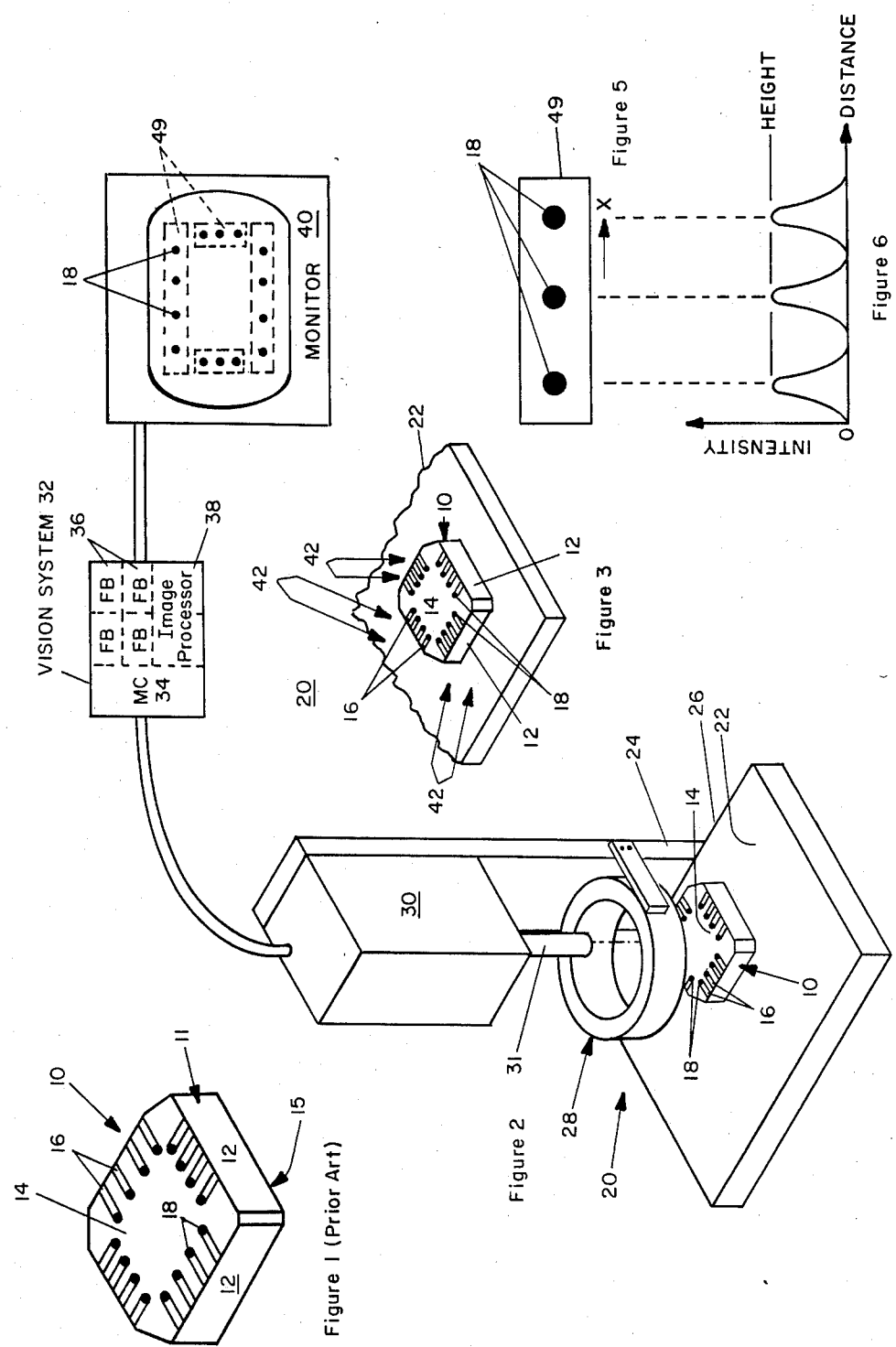

METHOD AND APPARATUS FOR INSPECTING ARTICLES

TECHNICAL FIELD

This invention relates generally to a method and apparatus for inspecting an article, such as a chip carrier having light reflective mesas on a planar surface thereof, to detect for the presence of defects.

BACKGROUND OF THE INVENTION

Recent efforts towards developing smaller size electronic components have led to the development of chip carriers which are comprised of a planar housing (e.g., ceramic) containing a semiconductor chip therein. Generally, there are two types of chip carriers, those having wire-like leads extending therefrom and those having no leads at all. Chip carriers which have no leads are designated as being "leadless". Instead of having leads, leadless type chip carriers have metallized pads on a major surface of the housing connected to the semiconductor chip therein.

In practice, leadless type chip carriers are mounted on a printed circuit board by placing the pads thereof in contact with metallized areas on a major surface of the printed circuit board. The metallized areas on the circuit board are arranged in the same pattern as that of the pads. Once the pads are in contact with the metallized areas on the printed circuit board, the pads are typically solder-bonded thereto. To facilitate bonding of the pads on the chip carrier to the metallized areas on the surface of the circuit board, typically, the pads are each provided with a deposit or bump of solder thereon. When reflowed, the solder bumps establish a solid mechanical and electrical connection between the pads and the metallized areas.

Typically, a spherical solder preform is bonded to each pad to provide the solder bump thereon. During the process of bonding the solder preform to each pad, defects can occur. For instance, the solder preform may not adhere to the pad, so that the pad will have no solder bump thereon. Also, during the bonding of the solder preforms to the pads, the preforms on adjacent pads may merge. Thus, the resultant solder bumps on the pads become bridged together, giving rise to an electrical short circuit. A defect may also exist if the solder bump on a particular pad is excessive (too large). A solder bump which is excessive may serve to bond the corresponding pad to more than one corresponding metallized area on the surface of the printed circuit board which is not desirable. On the other hand, a solder bump which is very small, due to poor reflow during the bonding of the preform to the pad, may not create a good bond between the pad and the metallized area.

In the past, chip carriers have been inspected visually by a human operator to detect defects such as missing, shorting or excessive solder bumps. Manual inspection of chip carriers is time consuming and is prone to inaccurate results. Even the most experienced human operator will miss, on average, 25% of the defects in a batch of chip carriers. Often two or more human operators are employed to inspect the same batch of chip carriers in order to assure a high degree of reliability. Further, multiple operations are often required simply to achieve required levels of production throughput. Using multiple operators to perform chip carrier inspection greatly increases overall production costs which is undesirable.

In an effort to avoid some of these difficulties, oftentimes only a small percentage of the chip carriers is actually inspected. Elimination of 100% inspection increases the chance that a chip carrier having some type of defect with regard to the solder bumps thereon may be mounted on a printed circuit board.

The task of visually examining the chip carrier for defects can be made easier by employing a video system of the type disclosed in U.S. Pat. No. 4,028,728 which issued June 7, 1977 to Benny H. Sharp and assigned to the instant assignee. The video system disclosed in the aforementioned patent comprises a polarized ring lamp which illuminates all sides of a planar article positioned therebeneath. A television camera, having polarized lens thereon, is positioned in registration with the ring lamp above the illuminated article. Only three-dimensional, light-reflective mesas, such as solder bumps, on the surface of the article serve to reflect the polarized light from ring lamp upwardly into the television camera. Thus, only the image of the solder bumps will be captured by the television camera. A video monitor is coupled to the television camera so that the operator can observe an enlarged image of the solder bumps on the video monitor without eye strain, thereby enabling more accurate article inspection.

The video system described in the aforementioned patent to Sharp may reduce the number of operators required to perform reliable article inspection, but will not eliminate the need for human operators entirely. A human operator is still required to analyze the image of the solder bumps displayed on the video monitor to determine if a defect is present.

Accordingly, there is a need for a technique for high speed, reliable automatic inspection of articles having light reflective mesas on a planar surface thereof to detect for defects.

SUMMARY OF THE INVENTION

The foregoing problems of the prior art are substantially overcome by the method of the present invention for inspecting an article having light reflective topographical features on a planar surface thereof to detect if defects are present therein. The method is initiated by illuminating the planar surface of the substrate with beams of light. The intensity of the light beams reflected upwardly from light reflective topographical features on the planar surface are then sensed. Thereafter, a one-dimensional profile of the intensity of the upwardly reflected beams of light is established as a function of distance along the surface of the article. The one-dimensional intensity profile is then analyzed to determine if defects are present in the light reflective mesas.

BRIEF DESCRIPTION OF THE DRAWINGS

FIG. 1 is a perspective view of a chip carrier according to the prior art;

FIG. 2 is a block diagram illustrating an apparatus for automatically inspecting the chip carrier of FIG. 1;

FIG. 3 is a perspective view depicting the illumination of the chip carrier of FIG. 1 by the apparatus of FIG. 2;

FIG. 5 illustrates a portion of the image of the chip carrier of FIG. 1 captured by the apparatus of FIG. 2; and FIG. 6 is a one-dimensional plot of the intensity of the image of FIG. 5 as a function of distance.

DETAILED DESCRIPTION

Figure 4:
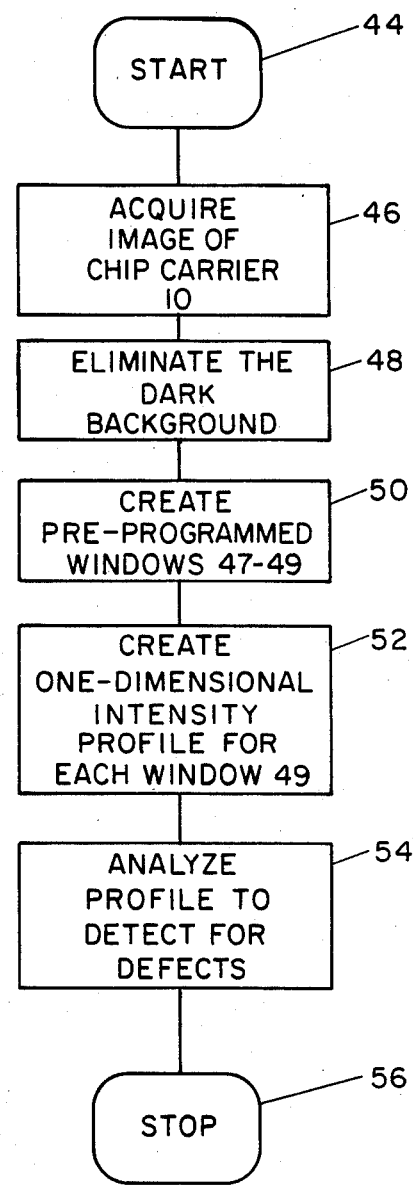
FIG. 4 is a flow chart illustrating a program executed by a processor within the apparatus of FIG. 2.

FIG. 1 is a perspective view of an electronic component known in the prior art as a chip carrier 10. The chip carrier 10 is comprised of a generally planar housing 11 (e.g., ceramic) which encloses a semiconductor chip (not shown). The housing 11 is typically square, having four sides 12—12 and first and second major surfaces 14 and 15 joined to the upper and lower edges of each of the sides. On the first surface 14 of the housing 11 is a plurality of parallel, spaced metallized pads 16—16, each typically plated with gold and connected by a thin wire lead (not shown) within the housing to the semiconductor chip. Typically, the pads 16—16 are arranged in four rows, the pads in each row being perpendicular to, and extending inwardly from, a separate one of the sides 12—12 towards the center of the surface 14.

To facilitate solder bonding of the pads 16—16 to the metallized areas on the printed circuit board (not shown), each pad typically has a generaly hemispherical bump 18 of solder deposited thereon. As the spherical solder preforms are bonded to the pads 16—16 to obtain the solder bumps 18—18, each pad is normally entirely wetted by the preform.

During the process of bonding the solder preforms to the pads 16—16 on the housing 11 to create the solder bumps 18—18, various defects can occur. For example, the solder preform may not bond to each of the pads 16—16 so there may be no solder bump 18 thereon. Further, the solder bumps 18—18 on two or more pads 16—16 may be bridged together as a result of the solder preforms merging during bonding to the pads. Those of the solder bumps 18—18 which are bridged together will give rise to an electrical short circuit between the corresponding pads 16—16 which is undesirable. Another type of defect occurs when one or more of the solder bumps 18—18 is excessive (too large). Each excessive solder bump 18 may serve to bond the corresponding pad 16 to which it is attached to more than one of the metallized areas on the printed circuit board which is not desirable. Difficulties may also arise when the solder bumps 18—18 are below a predetermined size due to insufficient wetting of the pads 16—16. Solder bumps which are too small may not serve to create a good bond between the pads 16—16 and the metallized areas on the circuit board.

Presently, inspection of the chip carrier 10 for defects is done visually by a human operator. Manual inspection often is not very effective. The small size of the pads 16—16 (typically, 0.018" by 0.040") and the small size of the solder bumps 18—18 (typically, 0.020" in diameter) makes it very difficult for a human operator, even using a microscope, to reliably inspect each chip carrier 10 for defects. Even the most experienced operator may miss as much as 25% or more of the defects. As a result, the chip carrier 10 which has passed inspection by an operator may, in fact, be defective. If this defective chip carrier 10 is later mounted on a printed circuit board, then the circuit board will likely be defective. From the standpoint of reducing repair and re-work costs, reliable inspection of each chip carrier 10 is very important.

FIG. 2 is a block diagram of an apparatus 20 for automatically inspecting the chip carrier 20 to detect defects thereon, such as missing and bridged solder bumps 18—18, as well as solder bumps which are too large or too small. The inspection apparatus 20 comprises a table 22 which supports the chip carrier 10 thereon so that the surface 14 is face-up. A support 24 is attached to an edge 26 of the table 22 and extends upwardly therefrom. A ring light 28 (e.g., a circular lamp attached to an annular reflector) is secured to the support 24 a short distance (e.g., 0.75") up from the table 22 to illuminate the chip carrier 10 thereon. A television camera 30, having a lens 31 thereon, is secured to the support 24 above the ring light 28 so that the lens on the camera is coaxial with the ring light. When the chip carrier 10 is placed on the table 22 within the circular area illuminated by the ring lamp, the television camera 30 captures the image of the surface 14 on the chip carrier and outputs an analog signal which is representative thereof.

The television camera 30 is coupled to a vision system 32 which, in an exemplary embodiment, comprises a model P256 vision system manufactured by IRI Corporation, Carlsbad, Calif. The vision system 32 includes a microcomputer (MC) 34, four frame buffers (FB's) 36—36 and an image processor 38. A television monitor 40 is coupled to the vision system 32 to display information produced thereby.

In operation, when the chip carrier 10 is placed on the table 22 beneath the ring light 28, beams 42—42 of light emanate from the ring light towards the surface 14 from all sides thereof so that each beam is at an angle with the surface. The solder bumps 18—18 on the surface 14 are generally hemispherical in shape and are very specular (light reflective), thus serving to reflect a portion of the light beams 42—42 impinging thereon vertically upwardly into the lens 31 on the television camera 30 of FIG. 2.

The pads 16—16 are also very specular, since they are typically wetted with solder. However, the pads 16—16 are substantially planar and, for the most part, the beams 42—42 which strike the pads at an angle will not be reflected vertically upwardly, towards the television camera 30. Also, substantially none of the beams 42—42 are reflected upwardly from the surface 14 surrounding the pads 16—16 because the surface is very diffuse and serves to scatter, rather than reflect, the light impinging thereon. As a consequence, the image of the surface 14 captured by the television camera 30 is brightest in the regions occupied by the solder bumps 18—18. The darkest part of the image corresponds to the area on the surface 14 not occupied by any of the pads 16—16.

Referring to FIG. 2, the analog output signal of the television camera 30, which is representative of the image of the surface 14 of the chip carrier 10, is processed by the vision system 32 to detect defects on the surface such as missing or bridged solder bumps 18—18 as well as those which are too small or too large. The manner in which the output signal of the television camera 30 is processed by the vision system 32 may be best understood by reference to FIG. 4, which is a flow chart illustration of a program which is executed by the microcomputer 34 to control the operation of the vision system. Referring to FIG. 4, the microcomputer 34 (FIG. 2) begins the program by executing a "start" step (step 44) during which time the microcomputer clears any previous data stored in the frame buffers 36—36 (FIG. 2). Next, the image of the surface 14 of the chip carrier 10 is acquired (step 46). The acquisition of the image of the surface 14 is accomplished by converting the analog output signal of the television camera 30 into a plurality of digital signals, each representing a small picture element (pixel) of the image. Each of these digital signals is then stored within the microcomputer 34.

Following step 46, all of the dark background within the image of the surface 14 is eliminated (step 48). The elimination of the dark background is accomplished by having the image processor 38 examine each pixel (which is represented by a corresponding one of the stored digital signals), to determine whether the intensity of the pixel is above a predetermined threshold value. Unless the intensity of the pixel is above the threshold value, the pixel is assigned an intensity value which would make it appear black when displayed on the monitor 40 of FIG. 2. When all of the dark background has been eliminated from the image of the surface 14, all that appears, when the image is displayed on the monitor 40 of FIG. 2, are the solder bumps 18—18.

After step 48, the image processor 38 of FIG. 3 creates four imaginary windows 49—49 (step 50) within the image of the surface 14, which is displayed on the monitor 40 of FIG. 2. Each window 49, which is represented in FIG. 2 as a dashed line, surrounds the area expected to be occupied by a corresponding row of solder bumps 18—18. Note that the solder bump 18 at the end of each row is enclosed in only one of the windows 49—49. FIG. 5 is an enlarged view of one of the two vertical windows 49—49 in FIG. 2. Because the dark background has previously been eliminated from the image of the surface 14 during step 48 of FIG. 4, only the image of the solder bumps 18—18 is visible in the window 49 of FIG. 5. After the windows 49—49 are created, data representative of the image enclosed within each window is stored in a corresponding one of the frame buffers 36—36 of FIG. 2.

For purposes of inspecting for defects on the surface 14, the only areas of interest are those where the solder bumps 18—18 are expected to be located. Thus, only the image data representative of these areas (which corresponds to the image data representative of the areas enclosed by the windows 49—49) is required for analysis purposes. In this way, the amount of image data representative of the surface 14 that must be processed to detect defects is reduced.

After step 50, the image processor 38 of FIG. 2 then proceeds to create a one-dimensional profile of intensity of the image within each of the windows 49—49 as a function of distance along the surface 14 of FIGS. 1-3 (step 52). The term one-dimensional is used to describe the intensity profile created during step 52 because the profile varies with a single quantity distance. To create each intensity profile, the image processor 38 integrates the image data stored in each of the frame buffers 36—36 of FIG. 2 along the width of the corresponding one of the windows 49—49, the width being the shorter of the two dimensions thereof.

FIG. 6 is a graphical representation of the intensity profile produced during step 52 of FIG. 4 of the image enclosed by the window 49 of FIG. 5. As may be seen from a comparison of these two figures, the peaks within the intensity profile of FIG. 6 correspond to the solder bumps 18—18 within the window 49 of FIG. 5. The valleys in FIG. 6 correspond to the regions between the solder bumps in FIG. 5.

Referring to FIG. 4, following step 52, the intensity profile of each window 49 of FIG. 5 is then analyzed to detect for defects (step 54) by examining the spacing and characteristics of the peaks therein. If, for example, one of the solder bumps 18—18 was missing one of the pads 16—16 of FIG. 1, then, there will be no corresponding peak within the intensity profile of FIG. 6 where the solder bump is expected. Should there be bridging between two or more solder bumps 18—18, then there will be no clearly defined valley between the peaks within the intensity profile. If any of the solder bumps 18—18 are excessive, then the peaks associated therewith will appear greater in height than the peaks associated with those of the solder bumps 18—18 which are of a predetermined size. Conversely, any solder bumps 18—18 which are of insufficient size will be represented by peaks within the intensity profile of FIG. 6 which are of a height smaller than the height of the peaks associated with the normally-sized solder bumps. Thus, by analyzing the magnitude and spacing between the peaks of the intensity profile of FIG. 6, various different kinds of defects can be detected. Once defect analysis has been completed, then, program execution stops (step 56).

In practice, the inspection apparatus of FIG. 2 was able to complete inspection of a chip carrier 10 having as many as thirty-two solder bumps 18—18 thereon in approximately one-half second, which is nearly three times faster than the fastest human operator can complete chip carrier inspection. Moreover, the inspection apparatus 20 of FIG. 2 was found to have a reliability rate of better than 95% as compared to the average reliability rate of 75% for experienced human operators.

With slight modifications, the inspection apparatus 20 of FIG. 2 can also inspect for poor reflow of the solder bumps 18—18 due to improper wetting of the pads 16—16. It has been found that if there is improper wetting of the pads 16—16, then the portion of the pad not wetted will appear as a bright rectangular gold image upon illumination of the surface 14 of the chip carrier 10 of FIG. 1 with a beam of light normal thereto. In order for the inspection apparatus 20 of FIG. 2 to detect for improper wetting of the pads 16—16, it is necessary to increase the height of the ring lamp 28 above the table 22 (typically, to 6"-8") so that the beams 42—42 striking the surface 14 are substantially normal thereto. The program of FIG. 4 must also be modified so that the intensity profile created during step 52 is obtained by integrating the intensity data within each corresponding frame buffer 36 along the length of each window 49, rather than along the width thereof as before. Poor wetting of the solder pads 16—16 will give rise to an intensity profile having a plurality of pairs of closely spaced peaks, the peaks of each pair corresponding to the intensity of light reflected from the solder peak and the gold rectangular pad not wet with solder. Good wetting of the pads 16—16 will give rise to an intensity profile similar to that shown in FIG. 6 having only single peaks, rather than pairs of peaks.

While the apparatus 20 has been specifically described for inspecting a chip carrier 10, the apparatus is also useful for inspecting other planar articles having light reflective topological features thereon. For example, the apparatus 20 has been employed successfully to inspect beam leaded integrated circuits on a semiconductor wafer.

It is to be understood that the various embodiments described herein are merely illustrative of the principles of the present invention. Various modifications may be made thereto by those skilled in the art which may embody the principles of the invention and fall within the spirit and scope thereof.

What is claimed is:

1. A method for inspecting an article having at least one light-reflective topographical feature on a planar surface thereof comprising the steps of:
   illuminating the planar surface of the substrate with light;
   sensing the intensity of the light reflected upwardly from the article;
   establishing a profile of the cumulative intensity of the upwardly reflected light along an inspection axis on the planar surface of the article by summing the magnitudes of the intensities along an axis orthogonal to said inspection axis; and
   analyzing said intensity profile to determine the existence and condition of each said topographical feature.

2. The method according to claim 1 wherein the planar surface of the article is illuminated by directing the light downwardly towards the surface from all sides thereof so that the light is at an acute angle with the surface.

3. The method according to claim 2 wherein the light is directed downwardly towards the surface from all side thereof by positioning the article below a ring lamp.

4. The method according to claim 1 wherein the intensity profile is analyzed for defects by examining the intensity profile for the presence of peaks and evaluating the characteristics thereof.

5. The method according to claim 1 wherein only the intensity of the light reflected vertically upwardly from predetermined regions of interest on the article is sensed.

6. A method of inspecting a chip carrier for the presence of light-reflective solder bumps on a major surface thereof comprising the steps of:
   illuminating the major surface of the chip carrier by directing light thereat at an acute angle therewith from all sides thereof so that only the light striking a light reflective solder bump on the major surface of the chip carrier is reflected upwardly;
   sensing the intensity of the upwardly reflected light;
   establishing a profile of the cumulative intensity of the upwardly reflected light along an inspection axis on the major surface of the chip carrier by summing the magnitudes of the intensities along an axis orthogonal to said inspection axis; and
   analyzing said intensity profile by examining for the presence of peaks therein and evaluating the characteristics thereof to determine the existence and condition of the solder bumps on the chip carrier.

7. The method according to claim 6 wherein the major surface on said chip carrier is illuminated by positioning the chip carrier within a ring lamp.

8. The method according to claim 6 wherein only the intensity of the beams reflected vertically upwardly from predetermined regions of interest on the major surface of the chip carrier is sensed.

9. An apparatus for inspecting an article having at least one light-reflective topographical feature on a planar surface thereof comprising:
   means for illuminating the planar surface of the article with light;
   means for sensing the intensity of the light reflected upwardly from the article;
   means, coupled to said sensing means, for establishing a profile of the cumulative intensity of the upwardly reflected light along an inspection axis on the planar surface of the article by summing the magnitudes of the intensities along an axis orthogonal to said inspection axis; and
   means, coupled to said establishing means, for analyzing the intensity profile to detect the existence and condition of each said topographical feature.

10. The invention according to claim 9 wherein said illuminating means comprises a ring lamp.

11. The invention according to claim 9 wherein said sensing means comprises a television camera.

12. The invention according to claim 9 wherein said establishing means and said analyzing means comprise a vision system.

13. Apparatus for inspecting a major surface of a chip carrier for the presence of light-reflective solder bumps thereon comprising:
   a platform for supporting a chip carrier so that the major surface thereof is face-up;
   a ring lamp supported by said platform a distance above said chip carrier for directing beams of light downwardly towards the surface of the chip carrier from all sides thereof, with each beam at an acute angle with the said surface of said chip carrier so that only the solder bumps on said surface reflect the beams of light upwardly;
   a television camera supported by said platform above, and in registration with, said ring lamp for sensing the intensity of the upwardly reflected beams of light and for producing an output signal which varies accordingly; and
   a vision system coupled to said television camera and responsive to the output signal thereof for establishing a profile of the cumulative intensity of the upwardly reflected light along an inspection axis on said surface of said chip carrier by summing the magnitude of the intensities along an axis orthogonal to said inspection axis and for analyzing said intensity profile to determine the existence and condition of said solder bumps by examining for the presence of peaks in the intensity profile and evaluating the characteristics thereof.

* * * * *